United States Patent [19]
Boiarski et al.

[11] Patent Number: 5,701,181
[45] Date of Patent: Dec. 23, 1997

[54] FIBER OPTIC DIFFUSE LIGHT REFLECTANCE SENSOR UTILIZED IN THE DETECTION OF OCCULT BLOOD

[75] Inventors: Anthony Boiarski, Columbus, Ohio; Andrew Dosmann, Granger, Ind.

[73] Assignee: Bayer Corporation, Elkhart, Ind.

[21] Appl. No.: 440,105

[22] Filed: May 12, 1995

[51] Int. Cl.$^6$ .................. G01N 21/47; G02B 6/04; G01J 3/46
[52] U.S. Cl. .................. 356/446; 385/121; 356/425; 250/227.2; 250/227.23; 250/227.29
[58] Field of Search .................. 356/425, 446; 250/559.16, 559.18, 227.2, 227.23, 227.24, 227.29; 385/116, 119, 121, 120

[56] References Cited

U.S. PATENT DOCUMENTS

| | | | |
|---|---|---|---|
| 3,709,612 | 1/1973 | Clemens | 356/425 |
| 4,022,534 | 5/1977 | Kishner | 356/446 |
| 4,026,693 | 5/1977 | Sato | 385/121 |
| 4,033,698 | 7/1977 | Demsky et al. | |
| 4,076,421 | 2/1978 | Kishner . | |
| 4,409,477 | 10/1983 | Carl | 385/121 |
| 4,525,630 | 6/1985 | Chapman | 356/446 |
| 4,552,458 | 11/1985 | Lowne . | |
| 4,636,082 | 1/1987 | Barry | 356/446 |
| 4,645,917 | 2/1987 | Penney et al. | 356/376 |
| 4,756,619 | 7/1988 | Gerlinger et al. | 356/446 |
| 4,937,764 | 6/1990 | Komatsu et al. | 356/446 |
| 4,948,256 | 8/1990 | Lin et al. | 356/446 |
| 5,039,225 | 8/1991 | Uekusa | 356/446 |
| 5,282,017 | 1/1994 | Kasindorf et al. | 356/446 |
| 5,313,542 | 5/1994 | Castonguay . | |

FOREIGN PATENT DOCUMENTS

| | | |
|---|---|---|
| 0177861 | 4/1986 | European Pat. Off. . |
| 0299314 | 1/1989 | European Pat. Off. . |
| 05080048 | 3/1993 | Japan . |

*Primary Examiner*—Frank G. Font
*Assistant Examiner*—Jason D. Vierra Eisenberg
*Attorney, Agent, or Firm*—Roger N. Coe

[57] ABSTRACT

A fiber optic diffuse light reflectance sensor is disclosed. The sensor employs illumination optical fibers to carry light emitted from a high-intensity, narrow bandwidth LED to a baffle in a readhead where the optical fibers reflect the light off of a reagent test strip. The illumination optical fibers are randomly oriented to create a more uniform light source. The light is reflected off of a pad on a reagent test strip to detect the presence of non-hemolyzed trace and hemolyzed occult blood. The reflected light must pass through another baffle to a bi-convex lens where it is focused onto a detection bundle of optical fibers. The detection bundle is optically coupled with a CCD, where the optical signal is converted to an electrical one for processing and analysis.

12 Claims, 1 Drawing Sheet

FIBER OPTIC DIFFUSE LIGHT REFLECTANCE SENSOR UTILIZED IN THE DETECTION OF OCCULT BLOOD

FIELD OF THE INVENTION

The present invention generally relates to the field of medical diagnostic equipment used in clinical chemistry. More particularly, the present invention relates to a sensor used in a visual imaging system that analyzes a light reflectance change associated with one or more test pad areas on a reagent test strip following contact thereof with a liquid specimen containing occult blood.

BACKGROUND OF THE INVENTION

Reagent test strips are widely used in clinical chemistry. A reagent test strip usually has one or more test areas (pads), and each test area is capable of undergoing a color or brightness change in response to contact with a liquid specimen. An analyte is reacted with the reagent strip in order to ascertain the presence of one or more constituents or properties of interest in the analyte. The presence and concentrations of these constituents of interest in the specimen are indicated by a change in the test strip when reacted with the analyte. Light reflected off of the reacted reagent test strip is analyzed to determine if the constituents of interest are present and in what quantity. Usually, this analysis involves a color comparison between the reacted test pad and a color standard or scale. In this way, reagent test strips assist physicians in diagnosing the existence of diseases and other health problems.

Reflected light comparisons made with the naked eye can lead to imprecise measurement. Today, reagent strip reading instruments exist that employ reflectance photometry for reading test strip changes. These instruments determine the color change of a test strip, but only with limited resolution. Color variations smaller than the resolution of current instruments can be critically important for diagnosis, yet undetectable with current instruments. For example, such an instrument can fail to detect traces of non-hemolyzed blood within a urine specimen. Reagents like the occult blood pad on a Multistix® 10 SG reagent strip of the type sold by Miles Inc., Diagnostics Division, of Elkhart, In. 46515 develop small colored spots when reacted with low concentrations of non-hemolyzed blood in urine. Concentrations at these levels are commonly referred to as non-hemolyzed trace (NHT).

After a urine specimen has contacted a test pad of the Multistix® 10 SG reagent strip, intact blood cells appear as tiny green blotches on the orange test area. Existing strip readers detect the overall color or brightness of the test pad and large green areas, but ignore the small areas of green associated with non-hemolyzed blood. Small areas of green create a spotted appearance indicating that non-hemolyzed cells in the urine have hemolyzed on the reagent test paper. Currently the NHT condition, i.e., 5 to 15 cells/µL (microliter), is not consistently reported, thus producing false negative readings by automated urinalysis instruments. Furthermore, in hospital environments, NHT occurs in approximately one of every 15 urine samples and is only detected about 50% of the time. Current detectors can detect NHT only down to about 15 red blood cells/µL, which is not sufficiently accurate for all medical diagnosis. This is important because presence of non-hemolyzed blood cells in occult blood is related to the likelihood of various renal and other disorders. For example, a more accurate NHT detector would be useful in detecting such renal diseases such as hematuria, hemoglobinuria and myoglobinuria. Thus, a higher resolution diffuse reflectance sensor is highly desirable as a diagnostic tool.

Resolution in current reflectance sensors is inherently limited because such sensors have only been capable of reading one field of view (FOV) of a reagent pad; meaning, the entire reagent pad is viewed with one sensor. The problem with one FOV is that valuable color reflectance information occurring in small areas is lost. For example, if the optics have a FOV that is limited to a pad area (typically 0.5 cm×0.5 cm(centimeters)), then the optics would not have the sensitivity to detect color reflectance changes of small area (typically 0.03 cm in diameter) within the FOV.

Some prior art inventions have tried to overcome the single FOV limitation with a variety of methods. One approach is to use a moving aperture with a smaller FOV. An example of a device with a moving aperture is Japanese Kokai Patent Application No. Hei 5[1993]-80048, filed Sep. 20, 1991 by Suzuki et al. The Japanese Application also discloses the use of a bundle of optical fibers to transmit light reflected from a reagent strip. However, the application describes using a reading device with a moving aperture to measure light transmitted by the optical fibers. A problem with this design is that either the pad or aperture must be precisely moved to scan the light reflected from the reagent pad through the optical fibers. Difficulties with precise mechanical translation of the pad or aperture negatively affects cost, reliability and resolution.

SUMMARY OF THE INVENTION

The present invention is a method and apparatus for providing higher resolution of diffuse light reflected from a reagent strip. The test pads on the reagent strip are reacted with an analyte. Light reflected off of the reagent strip is converted into electrical signals that can be analyzed with diagnostic equipment. More specifically, one embodiment of the present invention employs a randomly oriented illumination bundle of optical fibers to illuminate the reagent strip with diffuse light from a remote light source. A baffle and lens system focuses the diffuse light reflected off of the reagent strip into a detection bundle of optical fibers at a first end. The detection bundle's first end cross-section is shaped to generally match the reagent pad area as focused onto the first end. The detection bundle's opposite end is arranged linearly to couple optically with a linear array detector. The linear array converts the reflected light transmitted by the detection bundle of optical fibers into electrical signals for processing. A small reference bundle of optical fibers is optically coupled to the linear detector to create a reference signal. The reference signal is used to prevent significant drift in gain of the linear array detector. The capability of splitting off some of the light to create the reference signal is another advantage in using optical fibers in this way. In one embodiment the electronic signals are processed to ascertain the presence of hemolyzed or non-hemolyzed trace blood in the analyte. Further analysis on the electronic signals, for example to determine the quantity of hemolyzed or non-hemolyzed blood, is also performed.

Detection sensitivity is improved to allow NHT detection of even 2 red blood cells/µL. This is made possible in part by using slender optical fibers in the detection bundle which serve to break up the reflected light into small representative areas for separate detection and analysis. Furthermore, each optical fiber is coupled to multiple detectors to drastically decrease the field of view for each detector. Because each detector has a much smaller FOV, much smaller details can be ascertained, thus resolution is increased. The present invention provides improved cost, reliability and performance advantages over current systems.

BRIEF DESCRIPTION OF THE DRAWING

Other aspects and advantages of the invention will become apparent upon reading the following detailed description and upon reference to the accompanying drawing, in which.

DETAILED DESCRIPTION OF THE PREFERRED EMBODIMENT

Figure 1:
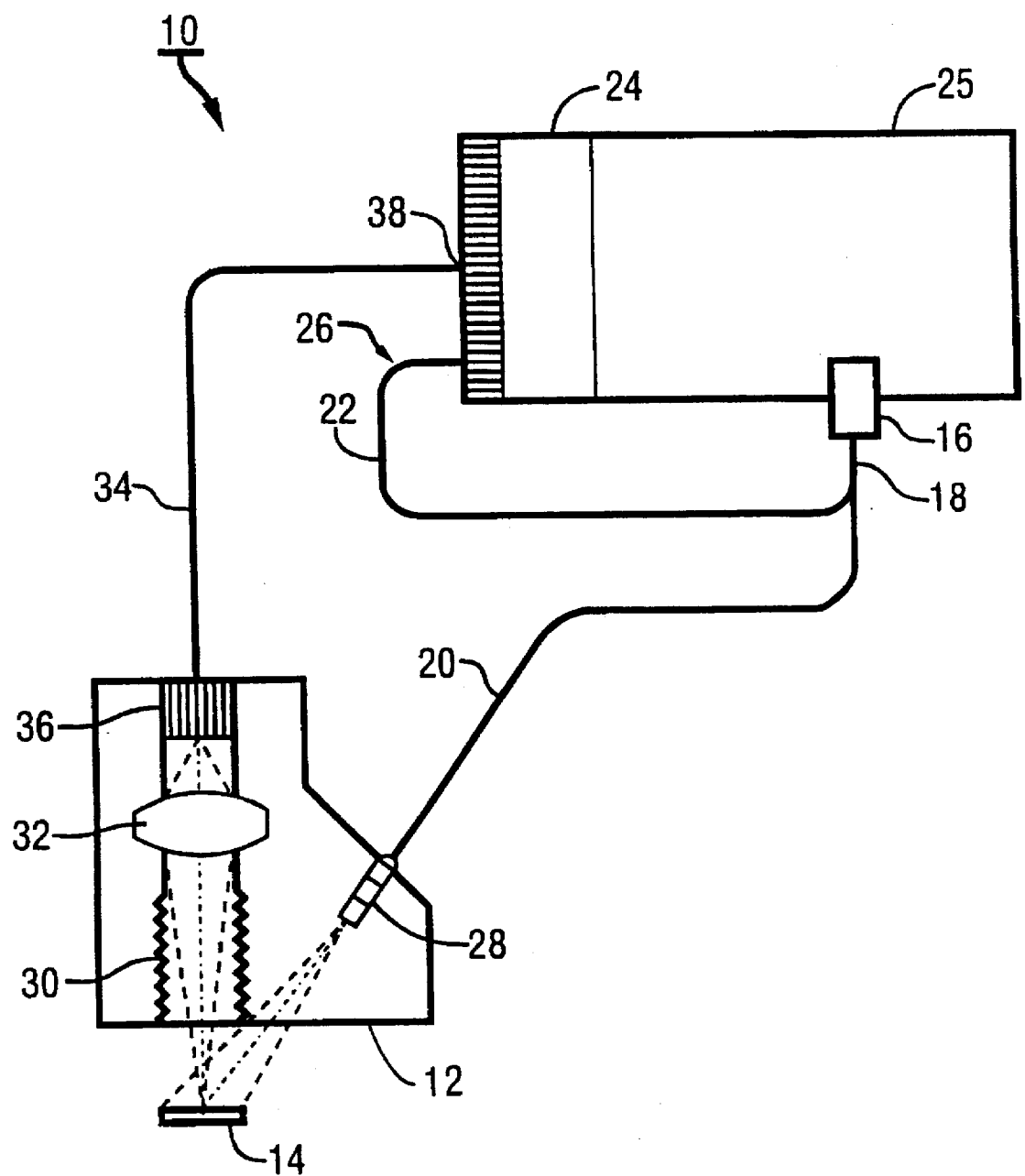
FIG. 1 is a block diagram overview of a fiber optic diffuse light reflectance sensor according to one embodiment of the present invention.

While the invention is susceptible to various modifications and alternative forms, a number of specific embodiments thereof have been shown by way of example in the drawings and will be described in detail herein. It should be understood, however, that this is not intended to limit the invention to the particular forms disclosed. On the contrary, the intention is to cover all modifications, equivalents and alternatives falling within the spirit and scope of the invention as defined by the appended claims.

An embodiment of the present invention is used in a medical diagnostic instrument to measure diffuse light reflected from reagent paper that has been reacted with an analyte, such as urine containing blood. Very small area color reflectance patterns are capable of detection with the present invention, particularly those of non-hemolyzed trace blood cells that develop during a chemical reaction between the reagent strip and the analyte.

In FIG. 1, a fiber optic diffuse light reflectance sensor 10 is designed with a readhead 12 to reflect light off of a reagent test strip pad 14 reacted with an analyte. The light reflected off the reagent test strip 14 originated at a light source 16. In one embodiment, the light source 16 is a single light emitting diode (LED) which emits light at a wavelength around 660 nm(nanometers), with a bandwidth of about ±13 nm and at a narrow angle (±5 degrees). For example, the TLRA180AP LED produced by Toshiba Corp., 1-1 Shibaura, 1-Chome, MinatoKu, Tokyo, 105-01, Japan, was found to be satisfactory as the light source 16. Note that other sources of light besides an LED may be used, such as a laser diode or a quartz halogen lamp combined with a narrow-band filter to provide monochromatic light. In one embodiment, the Toshiba LED has a desirable high intensity output of 3 mW(milliwatts)/cm$^2$ at a 20 mA(milliamps) drive current which is pulsed on and off using a constant-current pulsed direct current (DC) power supply. Pulsing the LED minimizes LED heating as well as associated LED intensity and wavelength variation.

Light emanating from the light source 16 is directed into a light-source optical fiber bundle 18. The light-source bundle 18 is comprised of hundreds of randomly oriented very thin optical fibers each approximately 0.01 cm in diameter. Note that the phrase "randomly oriented" does not require the optical fibers be absolutely random in orientation. The light-source bundle 18 is further divided into an illumination optical fiber bundle 20 and a reference optical fiber bundle 22. The reference bundle 22, which has an aggregate diameter of approximately 0.03 cm, is used to optically couple some of the light emanating from the light source 16 to part of a linear array detector 24. A number of pixels at one end of the linear array detector 24 are illuminated by the reference bundle 22 to provide a reference intensity signal 26. The reference intensity signal 26 is used to correct system drift caused by LED output or detector response variations over time. The reference bundle 22 therefore enables more consistent linear array detector 24 performance, which in turn produces greater measurement resolution of the fiber optic diffuse light reflectance sensor 10.

The illumination bundle 20 carries light from the light source 16 to an illumination light baffle 28 in the readhead 12. Light emanating from the illumination bundle 20 serves to illuminate each reagent strip pad 14 that is analyzed. The illumination bundle 20 has an approximate aggregate diameter of 0.28 cm and terminates within the illumination light baffle 28. The illumination light baffle 28 is mounted at a 30 degree angle with respect to a perpendicular axis of the reagent test strip pad 14, positioned adjacent the readhead 12, and serves to reduce stray light as well as improve uniformity of illumination over the reagent test strip.

Approximately 30 percent of the LED light is collected and transmitted by the illumination bundle 20. This light loss is mainly due to over filling the illumination bundle 20 input diameter by the LED output beam. Also the illumination bundle 20 numerical aperture (NA) is less than the LED output NA of 0.25. However, these optical inefficiencies provide for a more fault tolerant light source 16 to illumination bundle 20 alignment. Minor misalignment, including tilt of the LED, has minimal effect on illumination fiber bundle 20 illumination properties.

The reagent test pad 14 is illuminated with diffuse light emanating from the randomly oriented optical fibers of the illumination bundle 20 at an angle of 30 degrees. It has been shown that positioning the illumination optical fibers 20 in the readhead 12 at an angle of 30 degrees, as opposed to the 45 degree angle used in the prior art, improves illumination uniformity over the reagent test pad 14. Consequently, improved illumination uniformity produces a decrease in color reflectance sensitivity to variations in reagent strip pad 14 height. Sensitivity to height variations in the reagent pad 14 from the readhead 12 was reduced from 0.7% R/0.003 cm (prior art) to 0.2% R/0.003 cm. Prior art readheads typically illuminate test areas at an angle of 45 degrees. More consistent color reflectance values are achieved with illumination at 30 degrees than at 45 degrees because the cone of illumination reflected off the reagent test pad 14 expands and contracts more rapidly at the larger angle of illumination. The 30 degree illumination is therefore less sensitive to height and position variations in the reagent strip 14. Less height and position sensitivity facilitates a more precise measurement of the light reflected by the reagent strip 14.

The 30 degree illumination angle was selected because it provided the smallest practical angle. As described above, a small angle is more desirable in terms of providing a more uniform reagent pad 14 illumination intensity. The illumination baffle 28 has an aperture diameter of 0.36 cm positioned approximately 1.37 cm from the reagent test pad. These choices were made taking into account the illumination fiber bundle 20 NA to provide illumination of the entire reagent strip pad 14 including some over-illumination to account for pad 14/readhead 12 misalignment in the plane of the reagent test strip 14.

The illumination optical fiber bundle 20 employs a random optical fiber distribution, instead of other kinds of distributions such as direct (coherent) distribution, because of the more desirable features associated with random optical fiber distribution. For example, random fiber optic distribution, thus randomized illumination, provides a uniformity of reagent 14 illumination that varies by only ±15%. This configuration breaks up and more evenly distributes the non-uniform light created by the light source 16. Uniformity of illumination reduces variations in signal to noise of each small area color reflectance field of view detected. This improves precision of the reflectance measurements.

Furthermore, using optical fibers to illuminate the reagent pad 14 and carry light reflected from the reagent pad 14 has the advantage that the illumination source 16 is remotely located away from a sample area where reagent strips are analyzed. The optical fibers can be remotely illuminated with LEDs, laser diodes, or other light sources. Another advantage of fiber optic illumination is that the bundle 18 can be divided into a plurality of smaller bundles as needed.

After the diffuse light has been reflected off of the reagent strip 14, it passes through a detection light baffle 30 to a bi-convex lens 32. The detection light baffle 30 functions to reduce stray light entering the bi-convex lens 32. It was discovered that using a 2.08 cm long ×0.36 cm diameter cylindrical element to view the pad 14 and threading this element using a 0.164-32 UNC-2B thread design provided a suitable detection light baffle 30. Multiple reflections within the threaded region effectively absorbed unwanted light.

The lens 32 to pad 14 distance is preferably at least 0.84 cm. This displacement is necessary to prevent the detection light baffle 30 and lens 32 from being contaminated by sample on the pad 14. The detection light baffle 30 forms a 0.25 cm diameter aperture in front of the lens 32, thereby improving three performance factors. The aperture increases the f-number of the lens 32. An increase in f-number of the lens 32 reduces optical aberrations versus pad 14 height variation (i.e., improves depth of field or height sensitivity). The detection light baffle 30 restricts the FOV of the lens 32 to within the pad area 14. This helps to ensure that only pad 14 reflected light is imaged onto a detection optical fiber bundle 34. The detection light baffle 30 also reduces extreme off-axis light (stray light) from entering the bi-convex lens 32. Off-axis light originating from the illumination or ambient room light is trapped within the detection light baffle 30.

The bi-convex lens 32 collects the reflected light passing through the detection light baffle 30 and images it onto an input end 36 of a detection fiber optic bundle 34. In one embodiment of the present invention the bi-convex lens 32 has a focal length of 0.64 cm, a diameter of 0.64 cm and the lens 32 is located 2.54 cm from the reagent pad 14. The bi-convex lens 32 produces a 3× magnification, therefore, the reagent pad 14 image is enlarged by 3 times as it is projected onto the input end 36 of the detection optical fiber bundle 34. The bi-convex lens 32 magnifies and projects onto the input end 36 of the detection optical fiber bundle fiber 34 a spot size (from the reagent pad 14 surface) of 0.02 cm. Therefore, the ratio of NHT spot size to magnified image spot size is 2.0. The size of a feature detected on the reagent pad 14 is dependent on the diameter and number of detection fibers in the detection bundle 34 and magnification of the lens 32. A 2:1 fiber to spot ratio is desirable for reliable spot detection.

Like the light-source optical fiber bundle 18, the detection optical fiber bundle 34 is made up of hundreds of very thin optical fibers held together to form a bundle. Each individual optical fiber in the detection bundle 34 receives reflected light from a small field of view (FOV) without moving the pad 14 or detection bundle 34. This avoids misalignment problems. Optical fibers in the detection bundle 34 are assembled randomly in order to save costs. However, the detection bundle 34 can also be configured as a coherent assembly. At the input end 36 of the detection bundle 34, the optical fibers are bundled into a shape that matches that of the image of the reagent pad 14 as transmitted through the bi-convex lens 32. In one embodiment the input end 36 is square, however, the input end 36 of the detection fiber 34 can be constructed into various shapes, e.g., round, rectangle, etc., that are consistent with the shape of the reagent pad 14 or pattern being detected.

The readhead 12 mechanically holds the illumination and detection fiber optic bundles 20, 34 and baffles 28, 30 as well as the bi-convex lens 32 in alignment. The readhead 12 component can be molded or machined.

In one embodiment, the detection optical fiber bundle 34 uses 400 randomly oriented fibers that are each 0.01 cm in diameter. The 400 detection bundle 34 fibers are assembled into an approximately square (0.1 cm×0.1 cm) pattern at the input end 36 in order to match the square shape of the reagent test pad 14. The given input end 36 size, in conjunction with the lens magnification factor of 3 provides a 0.3 cm×0.3 cm magnified reagent pad 14 image. At an output end 38 of the detection bundle 34, i.e., the end in contact with the linear array detector 24, the detection bundle fibers 34 are arranged in a linear array 0.01 cm high×2.03 cm long.

The light output of the detection optical fibers 34 is averaged to determine the overall reflected intensity. This average color reflectance value indicates the presence of hemolyzed blood in the sample. Therefore, the sensor 10 detects both hemolyzed and non-hemolyzed blood levels in a urine sample.

At the output end 38 (opposite the input end 36) of the detection optical fiber bundle 34, the optical fibers are linearized into a ribbon or line. In one embodiment of the present invention the optical fibers are linearized in order to optically couple with the linear array detector 24. The fibers are mounted directly onto the face of the linear array detector 24. In an alternative embodiment the line of detection fibers 34 can be imaged with a lens (not shown) onto the linear array detector 24. Each fiber must have one or more corresponding detectors in the linear array 24 in order to maintain the maximum spatial resolution. Devices usable as the linear array detector 24 include charge coupled devices (CCDs), photocell arrays, color CCD arrays, or CMOS (complementary metal oxide semiconductor) photodiode arrays.

In one embodiment of the present invention a CCD is employed as the linear array detector 24. Each light sensing element within the CCD has an electrical response that is proportional to the light intensity received from the corresponding detection bundle 34 optical fiber. The electrical response is utilized by processing electronics 25. The processing electronics 25 serially clock out the electrical response of the array 24 into an analog to digital converter (not shown) which in turn converts the electrical response into corresponding digital data. The processing electronics 25 also include a microprocessor (not shown) which stores and utilizes the digital data to calculate contrast variations indicated by the individual detection elements in the linear array detector 24. The number and locations of contrast variations is used to determine a concentration of NHT or hemolysis in the analyte tested.

The CCD supports a 2,048-pixel array. For example, a commercially available CCD array from EG&G Reticon Inc., 35 Congress Street, Salem, Ma. 01970, was used in one embodiment of the present invention. This particular CCD uses pixels 14 μm(micrometers) wide by 130 μm high, providing 3.5 pixels per fiber and a 2.54 cm CCD length. With this arrangement the output intensity of each of the 400 fibers of the detection bundle 34 can be accurately recorded. Furthermore, additional space near the edge of the array 24 is available to record dark CCD pixel output from uncoupled pixels and the reference intensity signal 26 from the reference fibers 22. Dark CCD pixel output is used to correct pixel response intensity and is then combined with the detected reference intensity signal 26 to minimize detector 24 gain effects.

No transfer optics are required between the detection bundle's linear face 38 and the CCD because the direct contact method was selected. To accomplish this direct connection, the linear end 38 of the bundle 34 is bonded (e.g., by epoxy), directly to the CCD package face. An index matching material may also be placed between the output end 38 fibers and the CCD pixels to reduce light spreading. This arrangement facilitates a smaller sensor package. Furthermore, this arrangement produces an optimum CCD output modulation when recording the intensity of a darkened fiber (one observing an NHT spot) that exists next to a number of bright fibers (negative pad region).

One embodiment of the present invention has the following specifications:

Non-hemolyzed trace spot size diameter detection=<0.03 cm

Bi-convex lens 32 diameter=0.64 cm

Bi-convex lens 32 focal length=0.64 cm

Bi-convex lens 32 magnification=3

Bi-convex lens 32 field of view=0.3 cm×0.3 cm

Detection fiber optic bundle 34

Detection fiber 34 assembly is random

Number of fibers=400

Fiber diameter =0.01 cm

Fiber numerical aperture (NA)=0.25

Detection bundle input end 36 size=0.1 cm×0.1 cm

Detection bundle output end 38 size=2.03 cm×0.01 cm

Linear Array Detector 24 CCD array

Number of pixels=2048

Pixel width=14 µm

Pixel height=130 µm

Array length=2.54 cm

Thus, there has been described herein a fiber optic diffuse light reflectance sensor 10.

Obviously, many modifications and variations of the invention as hereinbefore set forth can be made without departing from the spirit and scope thereof and therefore only such limitations should be imposed as are indicated by the appended claims.

What is claimed is:

1. A fiber optic diffuse light reflectance sensor for detecting light reflected off of a reagent test pad reacted with a liquid specimen containing occult blood, comprising:

illumination means for providing light;

an illumination fiber optic bundle for receiving said light from said illumination means at an input end, said illumination fiber optic bundle transmitting said light through an output end of said illumination fiber optic bundle and reflecting said light off of said reagent test strip pad;

lens means for producing an image of said occult blood reacted with said reagent test strip pad by focusing said light reflected by said reagent test pad onto a plurality of optical fibers;

wherein said plurality of optical fibers form a detection optical fiber bundle having an input end for receiving said light focused by said lens means and an output end for emitting said light, said plurality of optical fibers at said input end of said detection optical fiber bundle being substantially arranged as an array to receive said image such that each optical fiber receives a portion of said image with a resolution, provided by said plurality of optical fibers, sufficient to provide detection of said occult blood, said plurality of optical fibers at said output end of said detection optical fiber bundle being arranged substantially linearly;

a linear array detector optically coupled to said output end of said detection optical fiber bundle, said linear array detector receiving said light emitted from said detection optical fiber bundle and converting said light into corresponding electrical signals; and interpretation means for interpreting color from said electrical signals.

2. The fiber optic diffuse light reflectance sensor of claim 1 wherein said illumination fiber optic bundle contains randomly oriented optical fibers.

3. The fiber optic diffuse light reflectance sensor of claim 1 wherein said illumination fiber optic bundle directs light to be reflected at an angle less than 45 degrees from an axis perpendicular to said reagent test pad.

4. The fiber optic diffuse light reflectance sensor of claim 3 wherein said angle is approximately 30 degrees.

5. The fiber optic diffuse light reflectance sensor of claim 1 wherein said reagent test pad has a shape, said input end of said detection optical fiber bundle being spatially oriented to approximate said shape of said reagent test area, said output end of said detection fiber optic bundle being linearly arranged.

6. The fiber optic diffuse light reflectance sensor of claim 1 wherein said linear array detector is comprised of a charge coupled device.

7. The fiber optic diffuse light reflectance sensor of claim 1 wherein said lens means further comprises a bi-convex lens.

8. The fiber optic diffuse light reflectance sensor of claim 1, wherein said illumination means for providing light further comprises a light emitting diode.

9. The fiber optic diffuse light reflectance sensor for detecting light reflected off of a reagent test pad reacted with urine, comprising:

a light source for providing said light;

an illumination fiber optic bundle, said illumination fiber optic bundle containing random optical fibers for carrying said light from said light source;

an illumination light baffle for receiving said light from said illumination fiber optic bundle;

a readhead for positioning said illumination fiber optic bundle to reflect said light off of said reagent test pad;

a detection light baffle receiving and transmitting said light reflected off of said reagent test pad;

a bi-convex lens receiving said light reflected from occult blood reacted with said reagent test pad and transmitted by said detection light baffle, said bi-convex lens focusing said light onto a detection fiber optic bundle formed by a plurality of optical fibers;

wherein said detection fiber optic bundle includes an input end for receiving light focused by said bi-convex lens, and a linear output end for transmitting said light, said plurality of optical fibers at said input end of said detection optical fiber bundle being substantially arranged as an array to receive said image such that each optical fiber receives a portion of said image with a resolution, provided by said plurality of optical fibers, sufficient to provide detection of said occult blood, said plurality of optical fibers at said output end of said detection optical fiber bundle being arranged substantially linearly; and a linear array detector optically coupled to said linearly organized output end of said detection fiber optic bundle, said linear array detector receiving said light transmitted from said detection fiber optic bundle and converting said light into corresponding electrical signals to thereby measure color.

10. The fiber optic diffuse light reflectance sensor of claim 9, wherein said linear array detector is further comprised of a charge coupled device (CCD).

11. The fiber optic diffuse light reflectance sensor of claim 9 wherein said light source is a light emitting diode (LED).

12. The fiber optic diffuse light reflectance sensor of claim 9 wherein said biconvex provides at least a three times magnification.

* * * * *